US010010481B2

(12) United States Patent
Gobbi Frattini

(10) Patent No.: US 10,010,481 B2
(45) Date of Patent: Jul. 3, 2018

(54) FLEXIBLE PACKAGE WITH A SEALED STERILE CHAMBER FOR THE RECONSITUTION AND ADMINISTRATION OF FLUID MEDICINAL OR NUTRITIONAL SUBSTANCES INSTILLABLE INTO THE BODY OF A PATIENT

(71) Applicant: Paolo Gobbi Frattini S.R.L., Milan (IT)

(72) Inventor: Paolo Guiseppe Gobbi Frattini, Sondalo SO (IT)

(73) Assignee: PAOLO GOBBI FRATTINI S.R.L., Milan (IT)

( * ) Notice: Subject to any disclaimer, the term of this patent is extended or adjusted under 35 U.S.C. 154(b) by 524 days.

(21) Appl. No.: 14/790,175

(22) Filed: Jul. 2, 2015

(65) Prior Publication Data

US 2016/0000650 A1 Jan. 7, 2016

(30) Foreign Application Priority Data

Jul. 2, 2014 (IT) .............................. MI2014A1201

(51) Int. Cl.
*A61B 19/00* (2006.01)
*A61J 1/14* (2006.01)
(Continued)

(52) U.S. Cl.
CPC ............... *A61J 1/1468* (2015.05); *A61J 1/10* (2013.01); *A61J 1/1406* (2013.01); *A61J 1/1412* (2013.01);
(Continued)

(58) Field of Classification Search
CPC .......... A61J 1/1468; A61J 1/10; A61J 1/1406; A61J 1/1412; A61J 1/1443; A61J 1/1475;
(Continued)

(56) References Cited

U.S. PATENT DOCUMENTS

| | | | | | |
|---|---|---|---|---|---|
| 4,410,321 | A | | 10/1983 | Pearson et al. | |
| 4,467,588 | A | | 8/1984 | Carveth | |
| 4,484,920 | A | | 11/1984 | Kaufman et al. | |
| 4,583,971 | A | * | 4/1986 | Bocquet ................ | A61J 1/2089 604/414 |
| 4,589,879 | A | * | 5/1986 | Pearson ................ | A61J 1/2089 604/410 |
| 5,766,147 | A | * | 6/1998 | Sancoff ................. | A61J 1/2089 141/2 |
| 2008/0269712 | A1 | * | 10/2008 | Oh ............................ | A61J 1/10 604/411 |

(Continued)

FOREIGN PATENT DOCUMENTS

| | | |
|---|---|---|
| EP | 0 395 758 A1 | 11/1990 |
| GB | 2 117 733 A | 10/1983 |

(Continued)

*Primary Examiner* — Tatyana Zalukaeva
*Assistant Examiner* — Ariana Zimbouski
(74) *Attorney, Agent, or Firm* — Jacobson Holman, PLLC.

(57) ABSTRACT

A package for infusion or instillation of medicinal or nutritional products into the body of a patient comprises a bag of liquid diluent equipped with at least one drain tube and a mixing tube equipped with a coupling and perforation device for a bottle of a pharmacological or nutritional substance in powder, gel or other material, provided with a perforatable cap. The package comprises a flexible airtight sterile casing, containing said bottle of the substance in powder or other and the coupling and perforation device. The bottle is housed in the casing in a coupling position with the coupling and perforation device and is manually manoeuvrable from the outside of the casing up to a perforating position of the cap of the bottle.

7 Claims, 13 Drawing Sheets

(51) Int. Cl.
*A61J 1/10* (2006.01)
*A61J 1/20* (2006.01)
*B65D 81/32* (2006.01)

(52) U.S. Cl.
CPC ........... *A61J 1/1443* (2013.01); *A61J 1/1475* (2013.01); *A61J 1/2089* (2013.01); *A61J 1/2093* (2013.01); *B65D 81/3216* (2013.01); *B65D 81/3266* (2013.01); *A61J 1/201* (2015.05); *A61J 1/2027* (2015.05); *A61J 1/2055* (2015.05); *A61J 1/2065* (2015.05)

(58) Field of Classification Search
CPC ... A61J 1/2089; A61J 1/2093; B65D 81/3216; B65D 81/3266
See application file for complete search history.

(56) References Cited

U.S. PATENT DOCUMENTS

| | | | | |
|---|---|---|---|---|
| 2009/0216184 | A1 | 8/2009 | Radmer et al. | |
| 2013/0281923 | A1* | 10/2013 | Gobbi Frattini .......... | A61J 1/10<br>604/85 |
| 2014/0352845 | A1* | 12/2014 | Lev ....................... | A61J 1/2089<br>141/329 |

FOREIGN PATENT DOCUMENTS

| | | | |
|---|---|---|---|
| JP | 2000-334042 | A | 12/2000 |
| WO | 2011/071952 | A2 | 6/2011 |

* cited by examiner

FLEXIBLE PACKAGE WITH A SEALED STERILE CHAMBER FOR THE RECONSITUTION AND ADMINISTRATION OF FLUID MEDICINAL OR NUTRITIONAL SUBSTANCES INSTILLABLE INTO THE BODY OF A PATIENT

The present invention relates to a flexible package with a sealed sterile chamber for the reconstitution and administration of fluid medicinal or nutritional substances injectable into the body of a patient.

BACKGROUND OF THE INVENTION

Packages for intravenous infusions or instillations are known, which comprise a flexible bag in which a chamber for containing a diluent is formed, and from which a flexible tube with an openable closure extends, equipped with a coupling and perforation device, through which a pharmaceutical or nutritional substance in powder, gel or other forms is withdrawn from a bottle and inserted into the inner chamber of the bag, which substance, once mixed with the diluent, forms the medicament or nutrient to be supplied to the patient.

It is increasingly required that the inner chamber of the flexible bag is made completely sterile. This is obtained by using machines which carry out the operations of filling and closing the bag in a sterile environment.

However, the problem of ensuring sterility conditions even when the bottle containing the medicinal or nutritional substance in powder is coupled to the tube extending from the flexible bag still remains.

By manually maneuvering the bottle and the tube, as currently occurs, a loss in sterility is inevitable, and in the case of particular high-risk drugs, this loss may lead to severe effects for both the patient and the medical and healthcare personnel responsible for the patient care.

First, there is the risk that an incorrect administration is performed, for example due to a premature or erroneous triggering of the drug reconstitution.

As it has been explained in the literature, the pharmacological therapy comprises the whole "chain" of the drug, i.e., all those actions and processes which are implemented to carry out the pharmacological therapy: this is a basic, crucial element of the health care.

A study dated 2003 (Taxis, 2003) showed, by directly observing the infusion therapy practice, that 73% of infusions are performed too fast, and that errors in the preparation occur in 14% of cases.

The most common errors are of various types: jeopardized sterility of the products to be mixed, unreadable writing of the data about the drug to be reconstituted on the infusion container, wrong cocktails of drugs, errors during the administration, etc.

With regard to potential risks for physicians, healthcare assistants, pharmacists, etc., the current drug reconstitution procedures include the use of special rooms equipped with protection systems (laminar flow hoods) and the personnel is subjected to strict safety measures. However, in the hospital facilities, pharmacists, physicians, healthcare assistants and other healthcare operators are subjected to a severe hazard for their health and reproductive capacity on a daily basis, often without even noticing it. Although the hazardousness of chemotherapy, antiviral drugs, antibiotics, hormones and other drugs is well characterized, estimation by the USA federal government confirm that over 5.5 million healthcare operators continue to be dangerously exposed to such substances every year.

Traces of hazardous drugs have been found on power outlets, chairs and tables, floors, and not only in hospital pharmacies, but also in patient rooms and other spaces intended to such pharmaceutical preparations.

Furthermore, several studies showed the presence of residues of hazardous drugs in the urine of the personnel responsible for the reconstitution of drugs.

BRIEF SUMMARY OF THE INVENTION

Hence, there is a need for a solution which allows a complete sterility to be ensured also during the reconstitution of the drug to be administered.

JP-A-2000334042 describes an aseptic medical syringe in which the mouth of a solvent-filled bag, a cylinder filled with a powdery drug, and a syringe piston usable to push the powdery drug out of the cylinder and into the solvent-filled bag are housed in a sterile manner within a sealed body. In order to mix the powdery drug with the solvent, it is necessary to open the sealed body, insert the syringe into the drug holding cylinder and finally actuate the syringe so as to push the powdery drug into the bag, where the mixing of the drug with the solvent occurs. Opening the sealed body for accessing the syringe contained therein clearly results in a loss of sterility and related risks, as explained above.

US-A1-2009216184 describes, in turn, a drug preserving and dispensing device which comprises two rigid cylindrical bodies telescopically coupled together so as to slide axially one into the other. One of the two rigid bodies, arranged at the bottom, forms a tank for a liquid diluent and includes a dispensing tube controlled by a valve, while the other body, arranged at the top, forms a housing for a bottle with a powdery drug which has a closing head facing the tank. A floating body is interposed between the tank and the bottle, having a perforated axial needle with two tips facing the bottle head and the floating body base, respectively. By pressing the upper body downwards, the two-tipped needle perforates both the bottle head and the floating body base, thus creating a communication between the bottle and the tank, whereby the liquid diluent may enter the bottle and be mixed with the powdery drug. By releasing the upper body, the thus-formed mixture inside the bottle may flow down into the tank, where the reconstituted drug is thus contained. Such a patent does not address the problem of sterilization.

EP 0 395 758 A1 describes a package for infusion or instillation of medicinal or nutritional products into the body of a patient, which comprises the features defined in the preamble of claim 1.

In the light of the sterilization problems set forth above and of the prior art represented by JP-A-2000334042 and US-A1-2009216184, and taking into account the teachings of EP 0 395 758 A1, it is the object of the present invention to provide the healthcare operators with a product which initially is under, and subsequently maintains completely sterile conditions.

According to the invention, such an object is achieved by a package for infusion or instillation of medicinal or nutritional products into the body of a patient, as generally defined in claim 1.

Thereby, the bottle with a substance in powder or other forms and the coupling and perforation device for mixing the two products and reconstituting the desired drug or nutrient remain within a sealed sterile casing, thus ensuring first the implementation and then the maintenance of a completely sterile condition, which allows the drawbacks and risks of the current art to be avoided.

Moreover, it is worth noting that the casing is flexible in order to allow the bottle to be maneuvered from the outside for the perforation of the cap with which it is provided for the reconstitution of the drug.

BRIEF DESCRIPTION OF THE SEVERAL VIEWS OF THE DRAWING(S)

Two embodiments of the package according to the present invention are shown by way of the example in the accompanying drawings, in which.

DETAILED DESCRIPTION OF THE INVENTION

Figure 1:
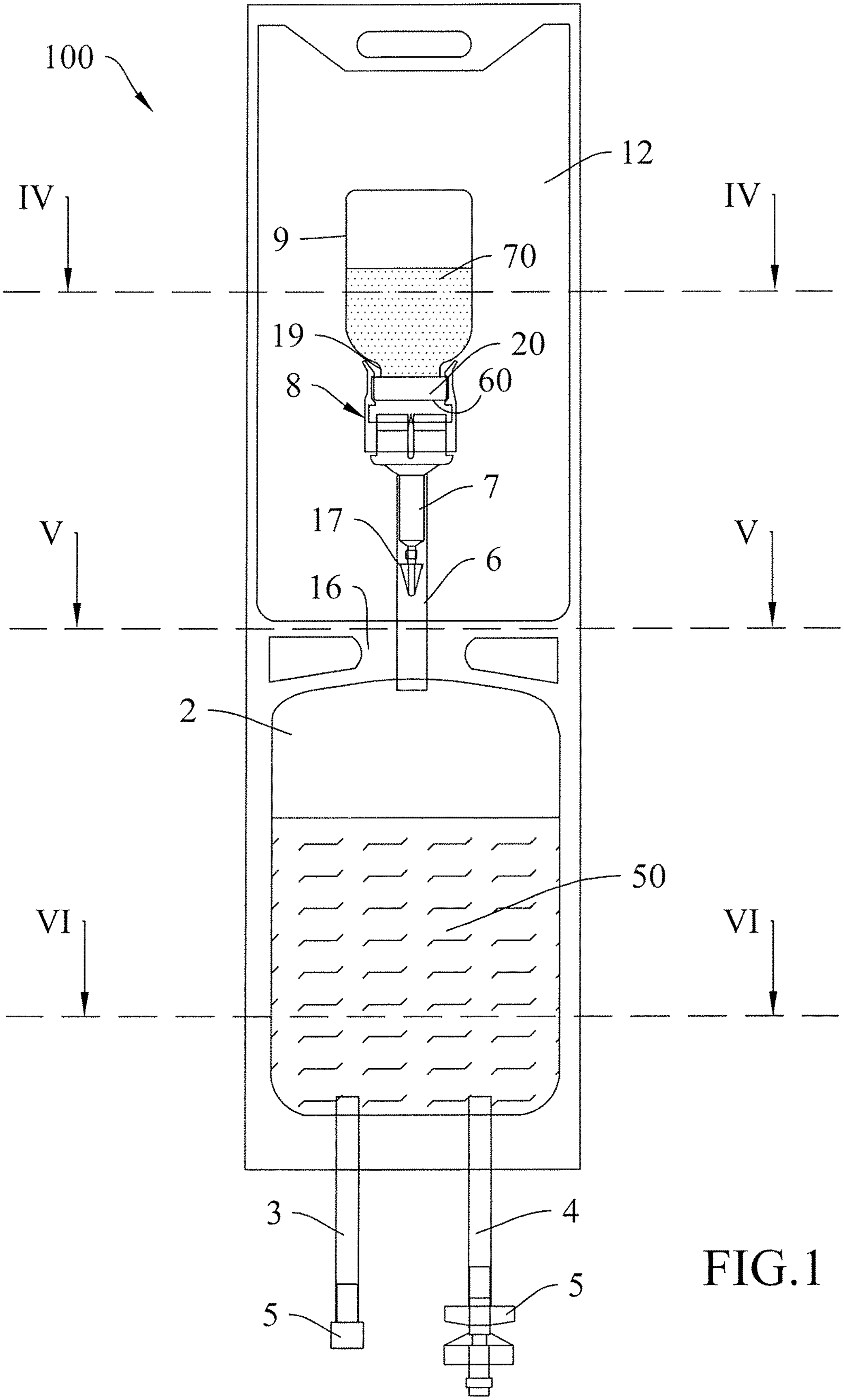
FIG. 1 shows a first embodiment of a package for infusion or instillation of medicinal or nutritional products into the body of a patient according to the present invention in a non-operative condition.
Figure 2:
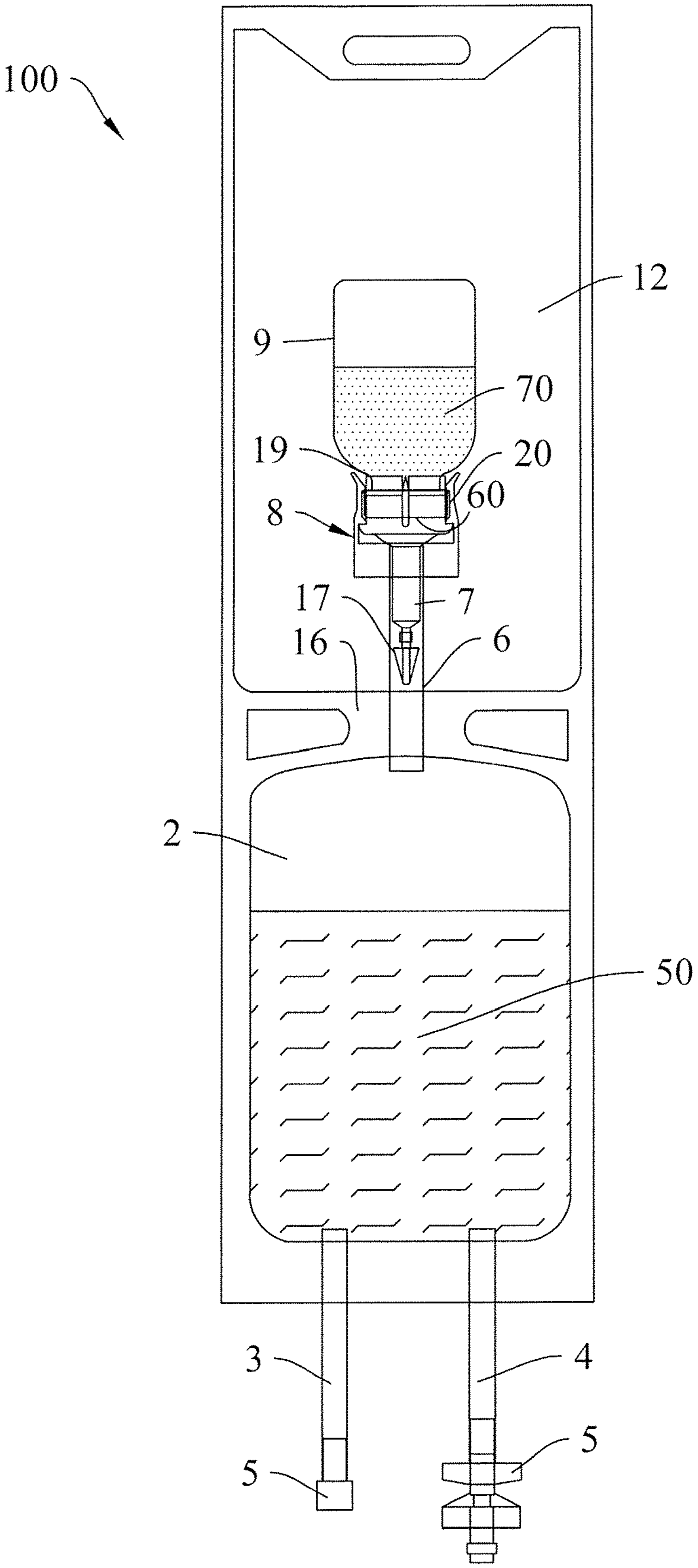
FIG. 2 shows the package in FIG. 1 in the perforating position of the bottle cap.
Figure 17:
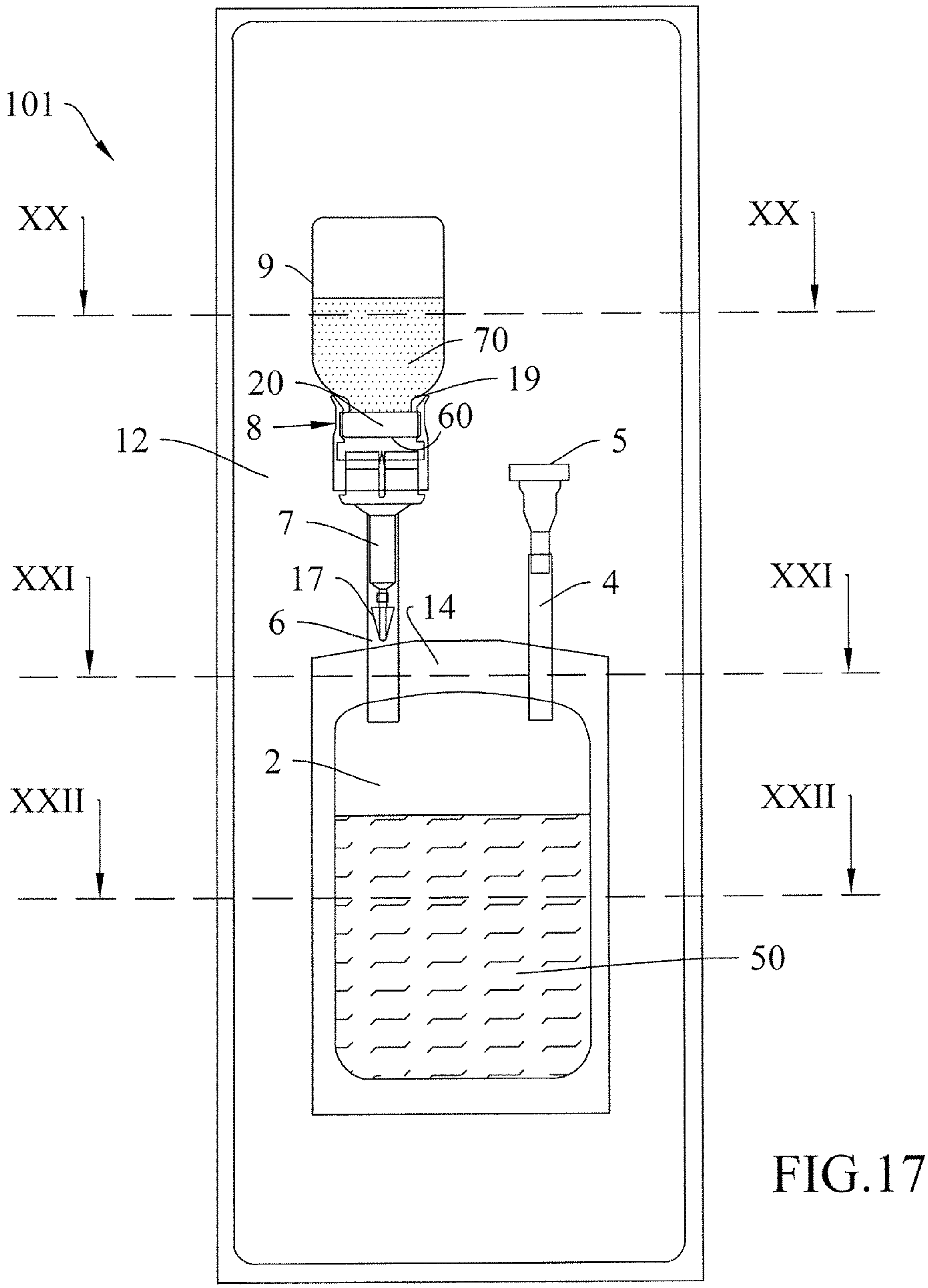
FIG. 17 shows a second embodiment of a package for infusion or instillation of medicinal or nutritional products into the body of a patient according to the present invention in a non-operative condition.
Figure 18:
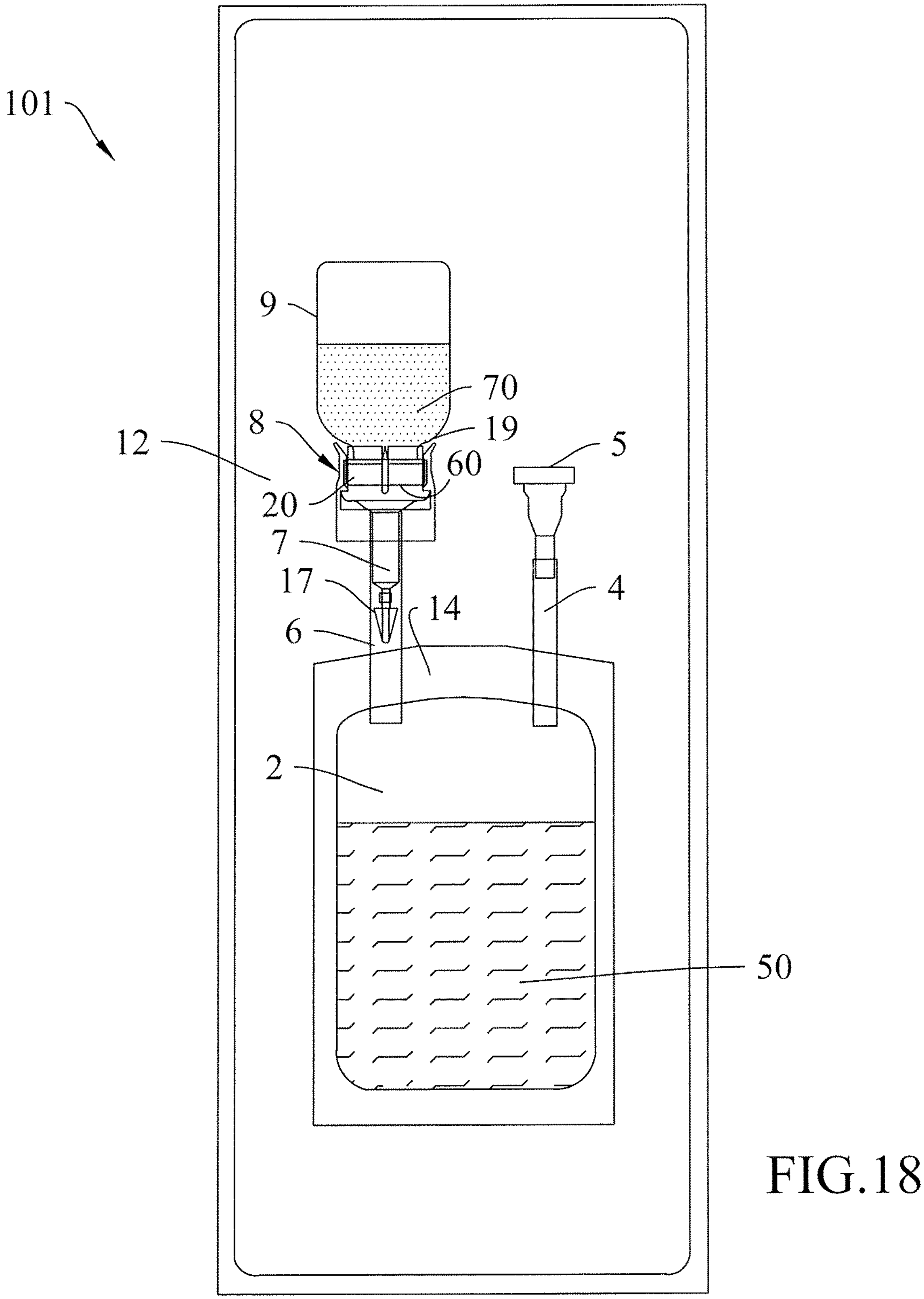
FIG. 18 shows the package in FIG. 17 after the perforation of the bottle.

FIGS. 1 and 17 show a first and a second embodiment, respectively, of a package 100, 101 according to the present invention for infusion or instillation of medicinal or nutritional products into the body of a patient.

Package 100 (FIG. 1) comprises a bag 2 of liquid diluent 50 equipped with at least one mixing tube 6, suitable to insert a pharmacological or nutritional substance 70 into bag 2, with at least one supply tube 3, suitable for the connection with a special infusion syringe (not shown in the Figures), and with at least one drain tube 4 with a coupling end for a catheter or infusion tubing, adapted to drain the solution consisting of the mixture of a pharmacological or nutritional substance 70 and liquid diluent 50 for infusion or instillation. Each of said supply and drain tubes 3, 4 is preferably flexible and ends with a closing device 5.

The administration of the mixed substance into the body of the patient typically occurs through a dripping chamber (not shown in the Figures), which prevents air from entering the blood stream, and further allows the flow of liquids to be assessed.

The mixing tube 6 is equipped with an openable closure 7 and ends with a coupling and perforation device 8 for a bottle 9 housed inside the package 100 and containing the pharmacological or nutritional substance in powder, gel or other material.

Figure 3:
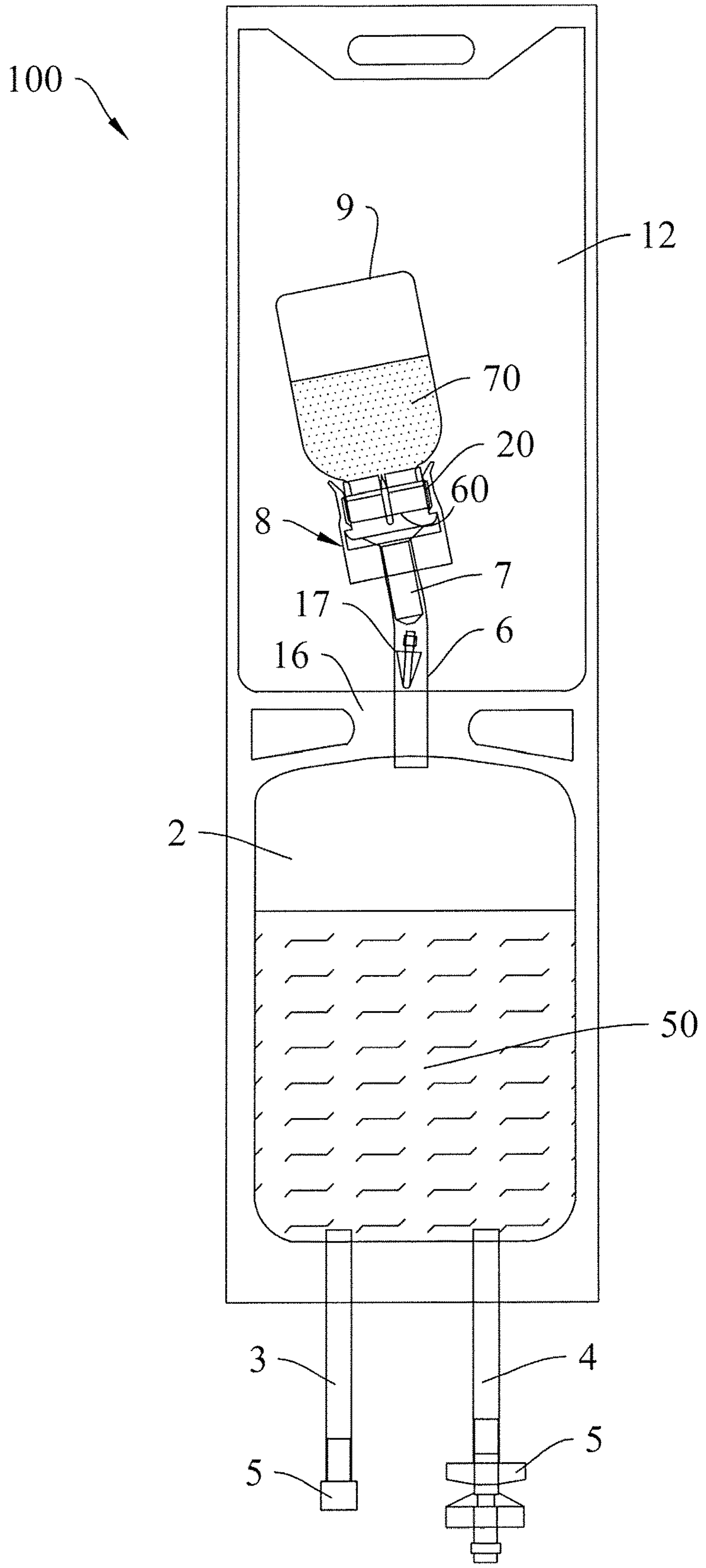
FIG. 3 shows the package in FIG. 1 during the transfer of an amount of base solution from the bag to the bottle for the transformation of the active powder substance into a liquid mixture.
Figure 4:
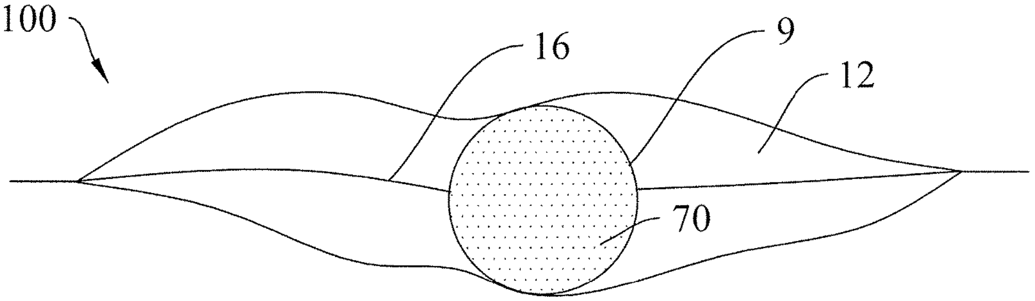
FIG. 4 shows a sectional view of the package in FIG. 1 according to line IV-IV.
Figure 5:
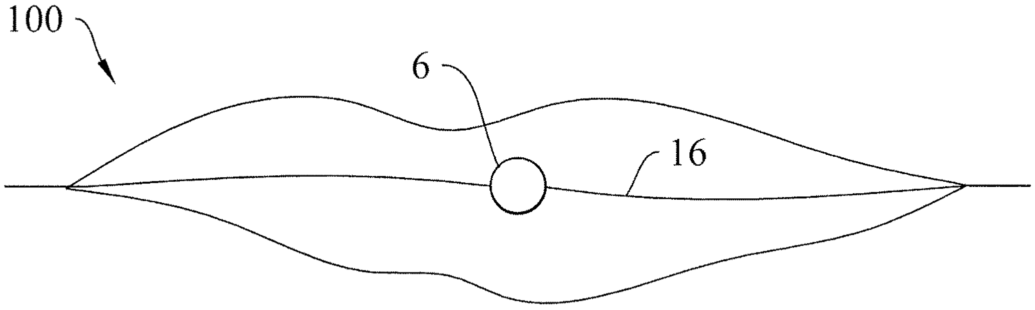
FIG. 5 shows a sectional view of the package in FIG. 1 according to line V-V.
Figure 6:
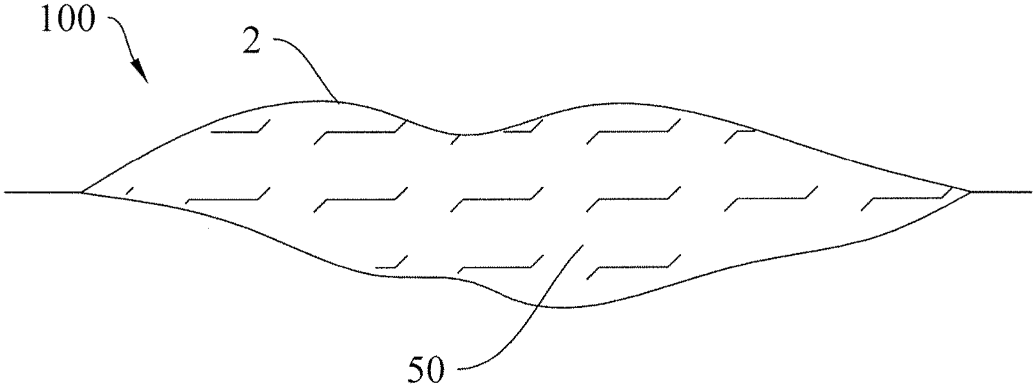
FIG. 6 shows a sectional view of the package in FIG. 1 according to line VI-VI.
Figure 7:
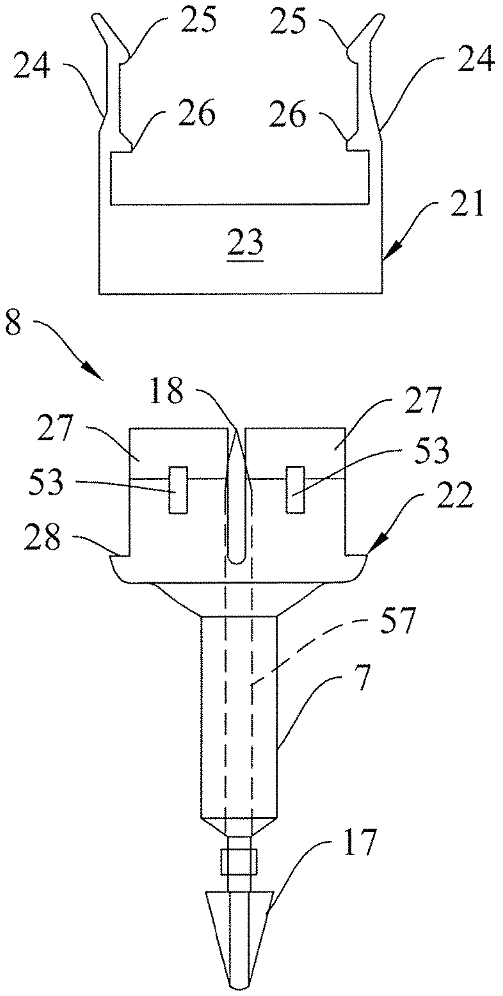
FIG. 7 shows a first view of a disassembled coupling and perforation element for the bottle.
Figure 8:
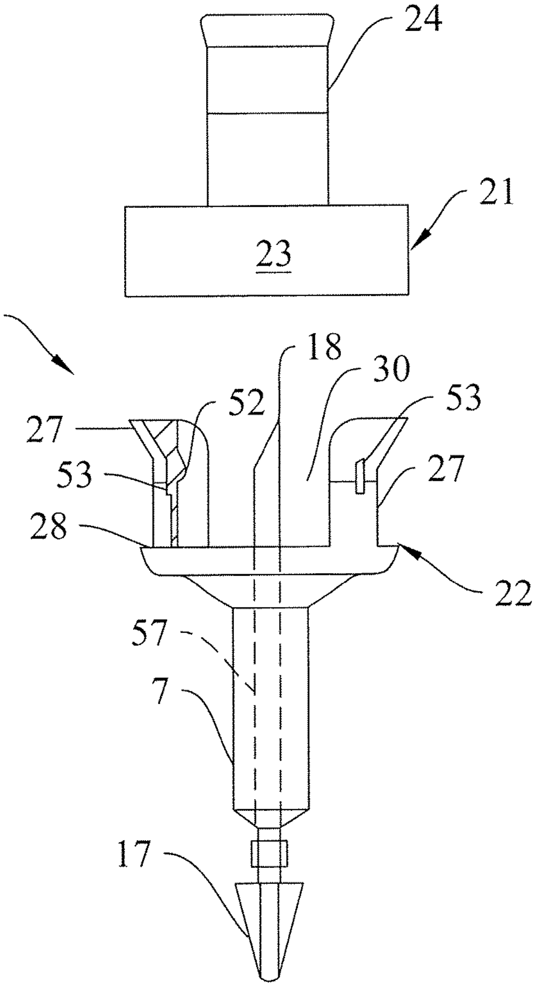
FIG. 8 shows a second view with a partial section of a disassembled coupling and perforation element for the bottle.
Figure 10:
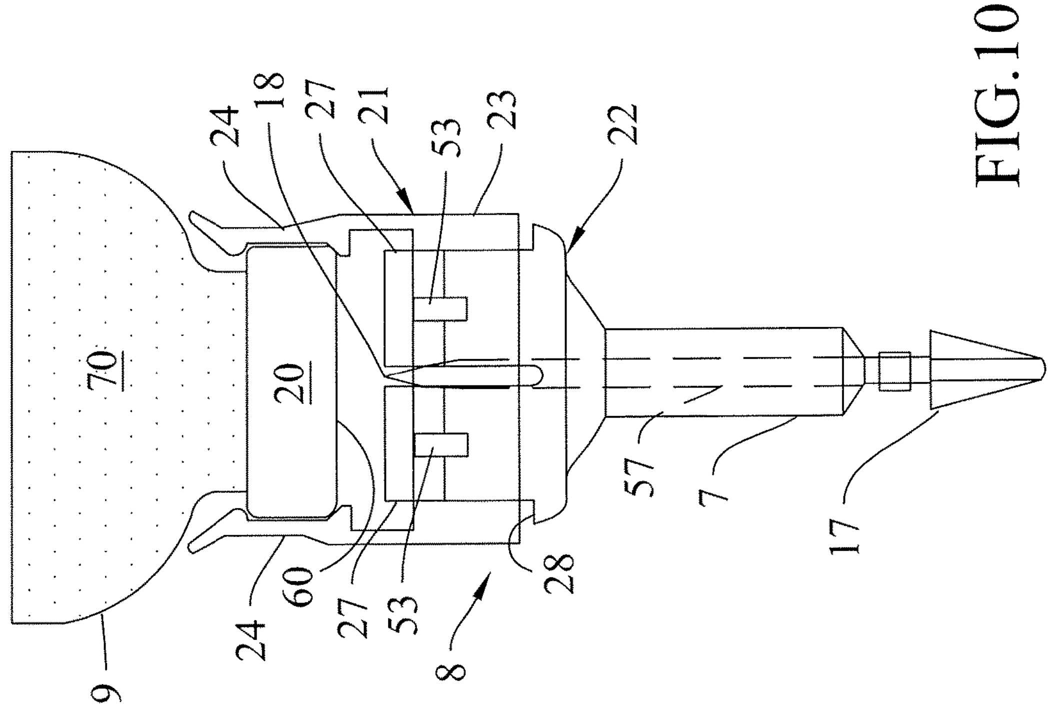
FIG. 10 shows a second view of the bottle in a coupling position with the coupling and perforation device.
Figure 9:
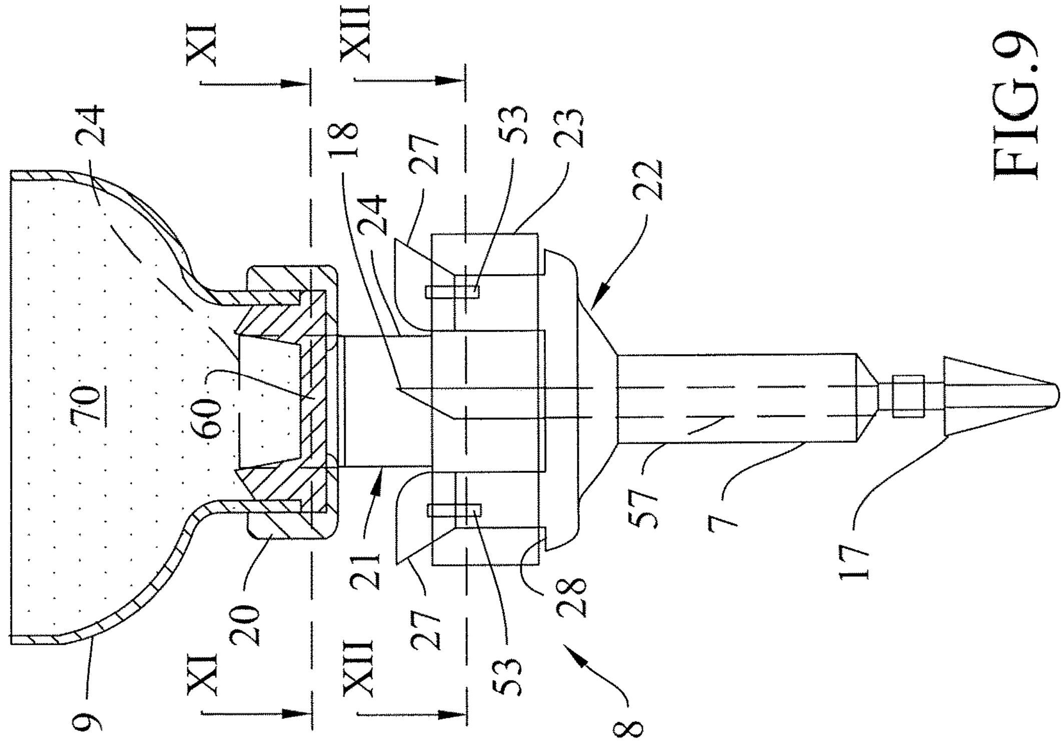
FIG. 9 shows a first view with a partial section of the bottle in a coupling position with the coupling and perforation device.
Figure 11:
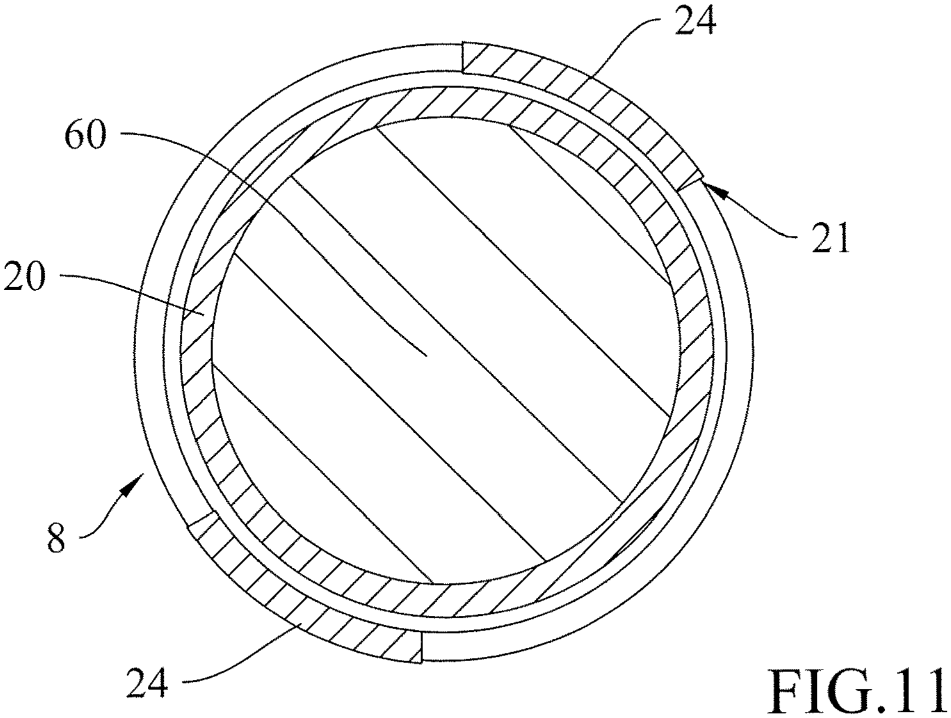
FIG. 11 shows a sectional view of the package in FIG. 9 according to line XI-XI.
Figure 12:
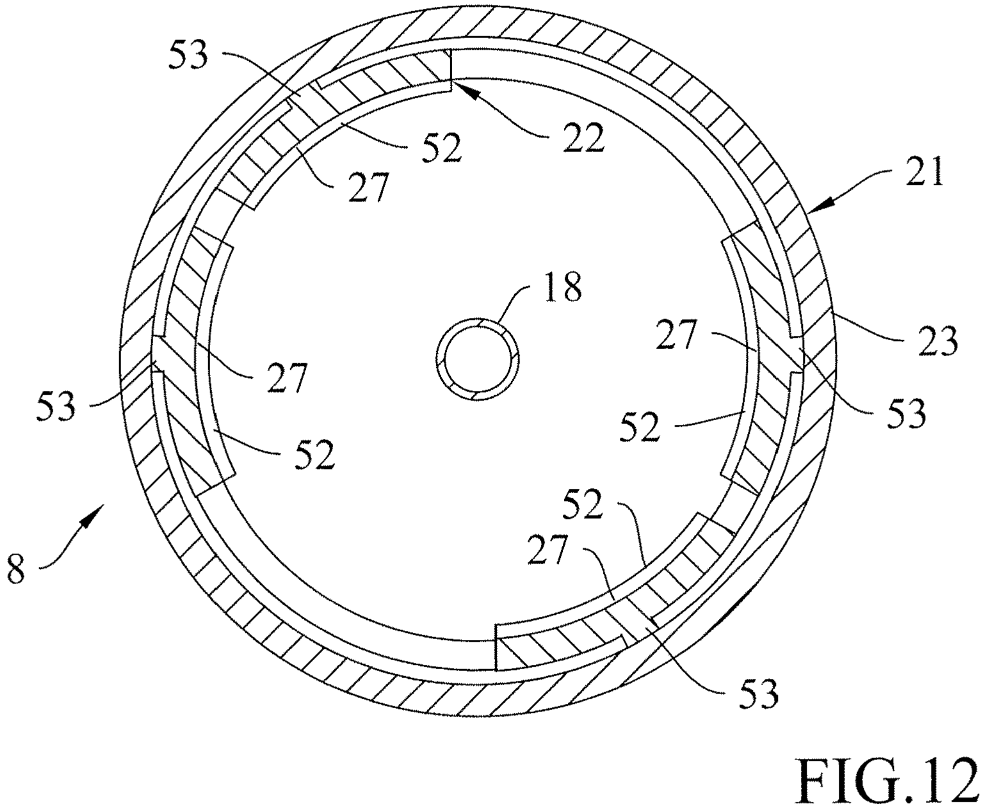
FIG. 12 shows a sectional view of the package in FIG. 9 according to line XII-XII.
Figure 14:
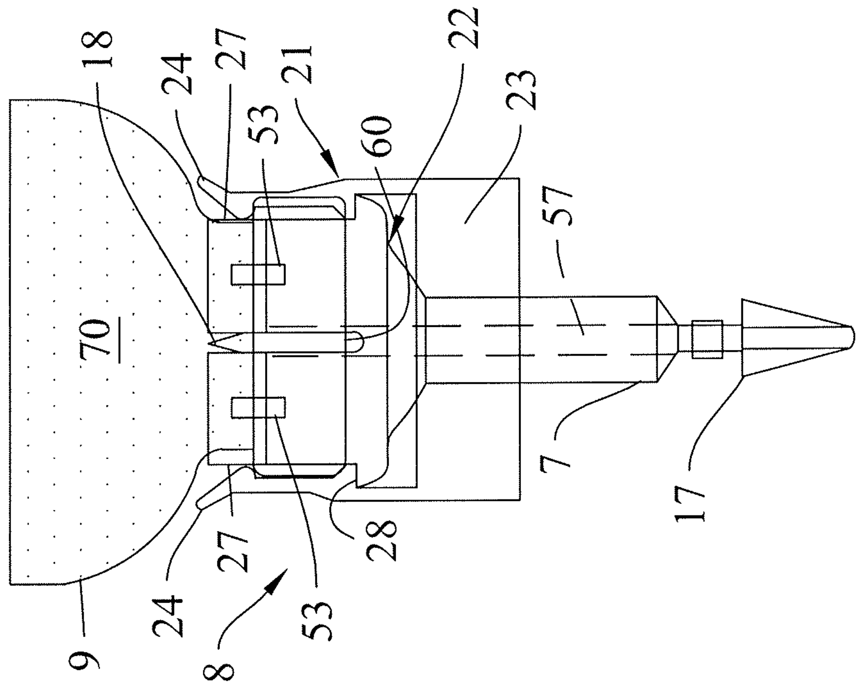
FIG. 14 shows a second view of the bottle in the perforating position of the bottle cap.
Figure 13:
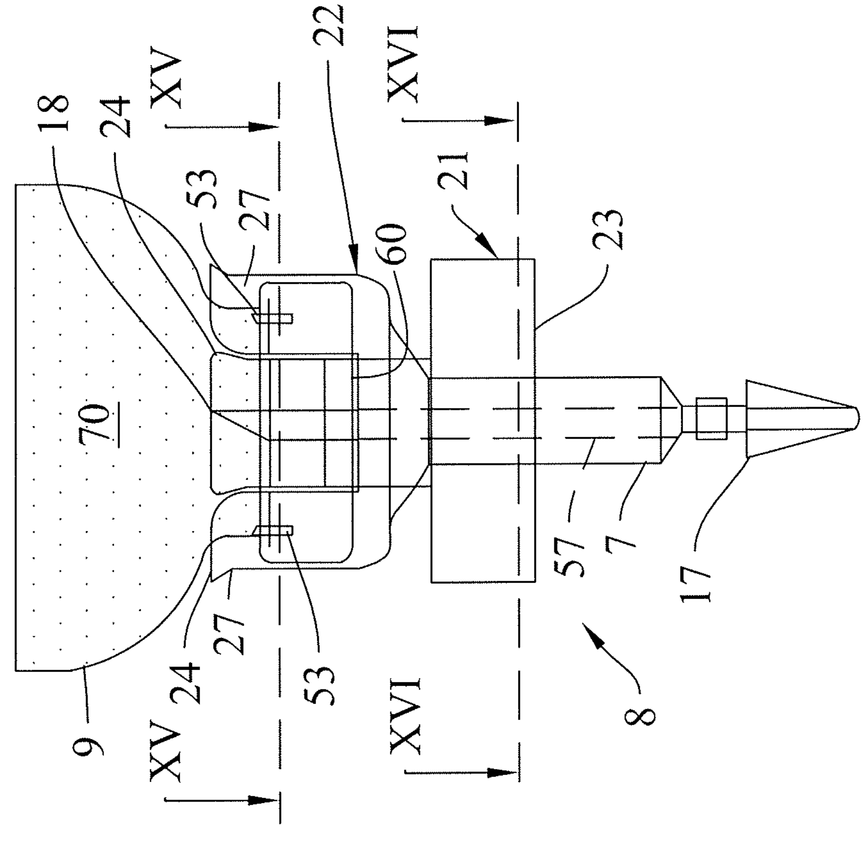
FIG. 13 shows a first view of the bottle in the perforating position of the bottle cap.
Figure 15:
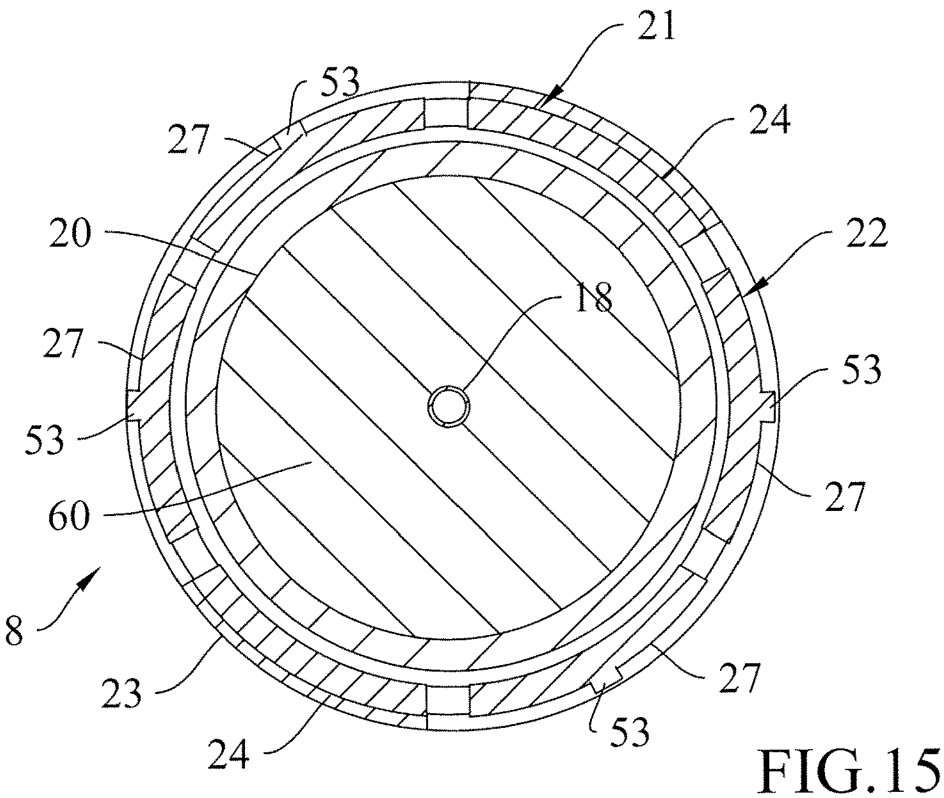
FIG. 15 shows a sectional view of the package in FIG. 13 according to line XV-XV.
Figure 16:
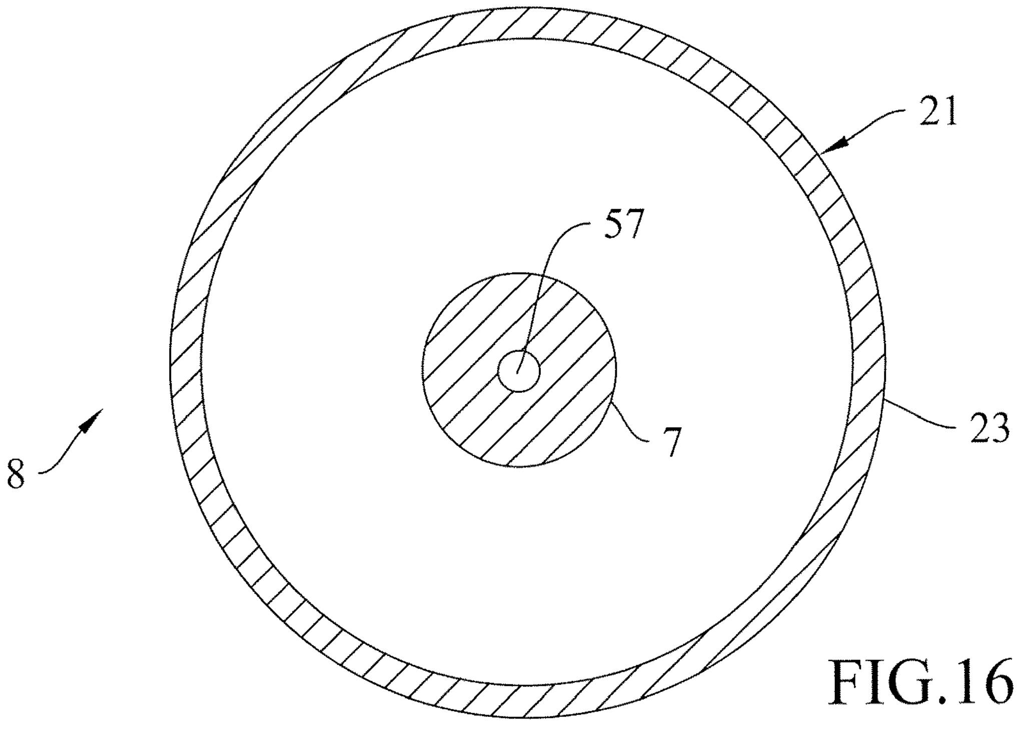
FIG. 16 shows a sectional view of the package in FIG. 13 according to line XVI-XVI.

The openable closure 7 is inserted into the mixing tube 6 and acts as a frangible cap therefor, having a tip-shaped initial portion 17, which is susceptible to be broken when manually bent as shown in FIG. 3. This operation opens the mixing tube 6 and allows the bottle 9 and the bag 2 of liquid diluent 50 to be put in communication for the insertion of the pharmacological or nutritional substance 70 in powder into bag 2.

In particular, the coupling and perforation device 8 comprises a first element 21 slidably coupled to a second element 22 and movable between the coupling position of bottle 9 and the perforating position of the cap 60 of bottle 9 (FIGS. 7-16).

The first element 21 (FIGS. 7, 8) comprises a ring 23 from which at least two flaps 24 vertically branch off, being equipped with notches 25, 26 adapted to accommodate bottle 9 in the coupling position.

The openable closure 7 of the second element 22 is surmounted by a circular base 28 from which pairs of further flaps 27, in turn equipped with notches 52 adapted to accommodate bottle 9 in the perforating position of cap 60, perimetrally branch off being placed vertically side by side. The second element 22 has gaps 30 between said pairs of further flaps 27. Said gaps 30 are located in correspondence of said at least two flaps 24 of the first element 21 and are adapted to accommodate the at least two flaps 24 with bottle 9 in the perforating position of cap 60.

Ring 23 is inserted outside said further flaps 27 (FIGS. 9-16) and is configured to slide coaxially with respect to the circular base 28. The further flaps 27 have a curvature at their free ends such as to form a first limit for the first element 21 in correspondence of bottle 9 in the coupling position, and the notches 26 are configured to contrast said circular base 28 and form a second limit of the first element 21 in correspondence of bottle 9 in the perforating position of cap 60.

Furthermore, in the outer walls of each of the further flaps 27 of the second element 22, locking notches 53 are present, which are adapted to lock the first element 21 in the coupling position of bottle 9. The thickness formed by the locking notches 53, by generating a friction with ring 23, reduces the mobility of element 21 when ring 23 is located in correspondence of the locking notches 53, thus stabilizing bottle 9 in the coupling position.

Bottle 9 comprises, in turn, a mouth 19 hermetically sealed by cap 60 made of an elastically deformable material, which is coupled to mouth 19 by means of a metal or plastic collar 20. In turn, the openable closure 7 of the coupling and perforation device 8 internally has a channel 57 ending at the top with a hollow tip 18 and at the bottom with the initial portion 17 which is frangible to allow the pharmacological or nutritional substance 70 in powder or other forms to pass from bottle 9 through the mixing tube 6 towards the bag 2 of liquid diluent.

Still referring to FIG. 1, package 100 comprises at least one flexible airtight sterile casing 12 containing said bottle 9 of the substance in powder or other forms and said coupling and perforation device 8.

Bottle 9 is housed in casing 12 in a coupling position with the coupling and perforation device 8 and, by virtue of the flexibility feature of casing 12, bottle 9 may be manually maneuvered from the outside of casing 12 up to a perforating position of said cap 60 through the coupling and perforation device 8 itself.

With reference to the FIGS. 1-6, the first embodiment 100 of a package for infusion or instillation of medicinal or nutritional products into the body of a patient is shown. In this first example, casing 12 is arranged in an aligned position with respect to the bag 2 of liquid diluent, and in particular they are vertically contiguous, so as to be hermetically separated by a single wall 16. Through such a wall 16, the mixing tube 6 for the communication between bottle 9 and bag 2 extends, in order to introduce the pharmacological or nutritional substance 70 in powder or other forms, contained within bottle 9, into bag 2. The modes for introducing the pharmacological or nutritional substance 70 in powder or other forms into bag 2 will be discussed below.

On the other hand, in FIGS. 17-22, the second embodiment 101 of a package for infusion or instillation of medicinal or nutritional products is shown. In this second example, casing 12 internally comprises the bag 2 of liquid diluent 50 with the drain tube 4 and the mixing tube 6 equipped with the coupling and perforation device 8 and the bottle 9.

Figure 19:
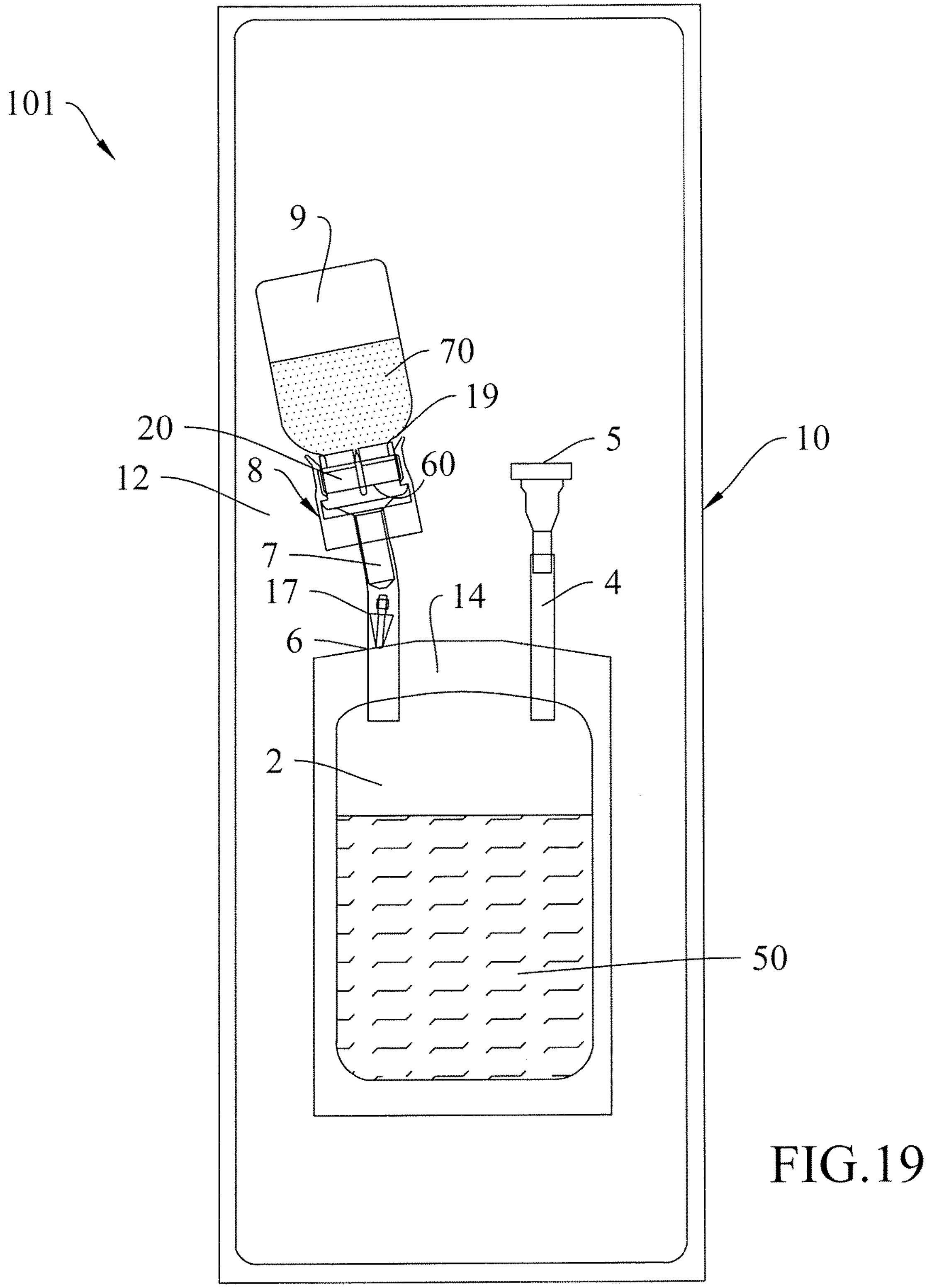
FIG. 19 shows the package in FIG. 17 during the transfer of an amount of base solution from the bag to the bottle for the transformation of the active powder substance into a liquid mixture.
Figure 20:
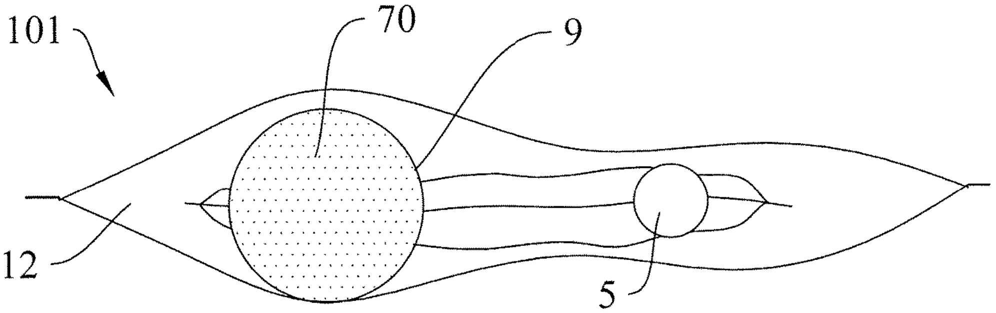
FIG. 20 shows a sectional view of the package in FIG. 17 according to line XX-XX.
Figure 21:
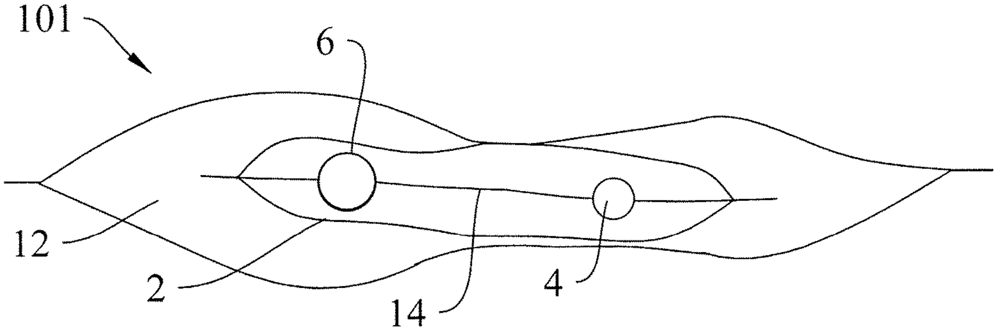
FIG. 21 shows a sectional view of the package in FIG. 17 according to line XXI-XXI.
Figure 22:
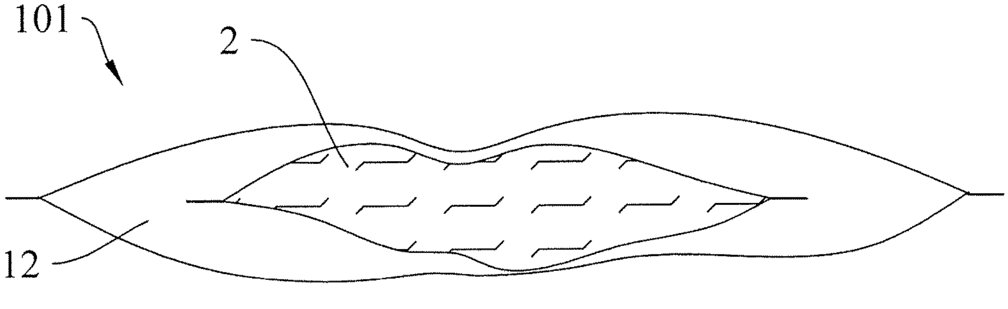
FIG. 22 shows a sectional view of the package in FIG. 17 according to line XXII-XXII.

In use, by virtue of the flexibility of casing 12, bottle 9 is manually maneuvered from the outside, starting from the coupling position with the coupling and perforation device 8 (FIGS. 9-12), up to the perforating position of cap 60 (FIGS. 13-16). In particular, bottle 9 is manually compressed from the outside until the notches 26 of ring 23 coaxially sliding with respect to the circular base 28 contrast the circular base 28 itself, and the hollow tip 18 perforates cap 60 for closing bottle 9. The portion 17 of the closing device 7 is then broken, whereby the liquid diluent 50 may flow from bag 2 into bottle 9 through channel 57 (FIG. 19).

Finally, maintaining the closing devices 5 of the supply and drain tubes 3, 4 (where the latter is present) closed, package 100, 101 is overturned several times to optimize the operation of carrying out and completing the mixing between the liquid diluent 50 and the pharmacological or nutritional substance 70 in powder or other forms.

Thereby, bottle 9 with the substance in powder or other forms and the coupling and perforation device 8 for mixing the two products and reconstituting the desired drug or nutrient remains inside the sealed sterile casing 12. Therefore, first the implementation and then the maintenance of a completely sterile condition are ensured, thus allowing the drawbacks and risks of the current art to be avoided.

The invention claimed is:

1. A package for infusion or instillation of medicinal or nutritional products into the body of a patient, comprising a bag of liquid diluent equipped with at least one drain tube, and a mixing tube equipped with an openable closure and with a coupling and perforation device for a bottle of a pharmacological or nutritional substance in powder, gel or other material, the bottle is provided with a perforatable cap, said package comprising at least a flexible airtight sterile casing, containing said bottle of the substance and said coupling and perforation device, said bottle being housed in the casing in a coupling position only with the coupling and perforation device and being manually manoeuvrable from the outside of the casing up to a perforating position of said cap through said coupling and perforation device, wherein said coupling and perforation device comprises a first element slidably coupled with a second element and movable between said coupling position of the bottle and said perforating position of the cap of the bottle, in which said first element comprises a ring from which at least two flaps equipped with notches suitable to accommodate the bottle in the coupling position, vertically branch off, and in that said openable closure is surmounted by a circular base from which pairs of further flaps, in turn equipped with notches suitable to accommodate the bottle in the perforating position of the cap, perimetrally and vertically side by sidebranch off, said second element having gaps between said pairs of further flaps in correspondence of said at least two flaps, said gaps being suitable to accommodate the at least two flaps with the bottle in the perforating position of the cap.

2. The package according to claim 1, wherein said ring is inserted externally to said further flaps and is configured to slide coaxially with respect to the circular base, and that said further flaps have a curvature at their free ends such as to constitute a first limit to said first element in correspondence of the bottle in the coupling position, and said notches are configured to contrast with said base circular and form a second limit to said first element in correspondence of the bottle in the position of perforation of the cap.

3. The package according to claim 1, wherein said further flaps of the second element comprise externally locking notches suitable to lock the first element in coupling position of the bottle.

4. The package according to claim 1, wherein said openable closure of the mixing tube has internally a channel ending at the top with a hollow tip and inferiorly with an initial portion which is frangible to allow passage of the pharmacological or nutritional substance from the bottle, through the mixing tube towards the bag of liquid diluent.

5. The package according to claim 1, wherein said casing is arranged in a position aligned with said bag of liquid diluent so as to be hermetically separated by a single wall, said mixing tube being configured to extend through said single wall for the communication between said bottle and said bag in order to introduce inside the bag the pharmacological or nutritional substance contained within the bottle.

6. The package according to claim 1, wherein said bag of liquid diluent is provided with a supply tube.

7. The package according to claim 1, wherein said casing comprises internally said bag of liquid diluent with said drain tube and said mixing tube equipped with the coupling and perforation device and the bottle.

* * * * *